(12) United States Patent
Brighton et al.

(10) Patent No.: US 7,215,995 B2
(45) Date of Patent: May 8, 2007

(54) METHOD AND DEVICE FOR TREATING OSTEOARTHRITIS AND CARTILAGE DISEASE, DEFECTS, AND INJURIES IN THE HUMAN HIP

(75) Inventors: Carl T. Brighton, Malvern, PA (US); Solomon R. Pollack, North Wales, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 7 days.

(21) Appl. No.: 10/987,866

(22) Filed: Nov. 12, 2004

(65) Prior Publication Data

US 2005/0177203 A1    Aug. 11, 2005

Related U.S. Application Data

(60) Provisional application No. 60/535,734, filed on Jan. 9, 2004, provisional application No. 60/520,088, filed on Nov. 14, 2003.

(51) Int. Cl.
*A61N 1/00* (2006.01)
(52) U.S. Cl. .......................................................... 607/2
(58) Field of Classification Search ............... 607/2, 607/46, 48–52, 65
See application file for complete search history.

(56) References Cited

U.S. PATENT DOCUMENTS

| | | | |
|---|---|---|---|
| 4,430,999 A | 2/1984 | Brighton et al. | 128/419 |
| 4,442,846 A | 4/1984 | Brighton et al. | 128/784 |
| 4,467,808 A | 8/1984 | Brighton et al. | 128/419 F |
| 4,467,809 A | 8/1984 | Brighton | 607/51 |
| 4,487,834 A | 12/1984 | Brighton | 435/173 |
| 4,506,674 A | 3/1985 | Brighton et al. | 128/419 |

(Continued)

FOREIGN PATENT DOCUMENTS

| | | |
|---|---|---|
| WO | WO 00/02585 A1 | 1/2000 |
| WO | WO 01/62336 A1 | 8/2001 |
| WO | WO 2005/070136 A2 | 8/2005 |

OTHER PUBLICATIONS

Chang, W.H., et al., "Enhancement of fracture healing by specific pulsed capacitively-coupled electric field stimulation," *Frontiers Med. Biol. Engng.*, 1991, 3(1), 57-64.
Aaron, R.K., et al., "The conservative treatment of osteonecrosis of the femoral head," *Clin. Orthop.*, 1989, 249, 209-218.
Aaron, R.K., et al., "Stimulation of experimental endochondral ossification by low-energy pulsing electromagnetic fields," *J. Bone Miner. Res.*, Nov. 2, 1989, 4, 227-233.

(Continued)

*Primary Examiner*—George Manuel
(74) *Attorney, Agent, or Firm*—Woodcock Washburn LLP

(57) ABSTRACT

A method of determining the voltage and current required for the application of specific and selective electric and electromagnetic signals to diseased articular cartilage in the treatment of osteoarthritis, cartilage defects due to trauma or sports injury, or used as an adjunct with other therapies (cell transplantation, tissue-engineered scaffold, growth factors, etc.) for treating cartilage defects in the human hip joint and a device for delivering such signals to a patient's hip. Anatomic, analytical, and planar circuit models are developed to determining the impedances, conductivities, and current flows in the human hip joint and its surrounding soft tissues and skin that are required to produce a 20 mV/cm electric field in the synovium and articular cartilage of the human hip. The voltage of the signal applied to the surface electrodes or to a coil(s) or solenoid is varied based on the size of the hip joint; larger hip joints require larger voltages to generate the effective electric field.

28 Claims, 6 Drawing Sheets

ANATOMIC MODEL

U.S. PATENT DOCUMENTS

| | | | |
|---|---|---|---|
| 4,509,520 A | 4/1985 | Dugot | 128/419 |
| 4,535,775 A | 8/1985 | Brighton et al. | 128/419 |
| 4,549,547 A | 10/1985 | Brighton et al. | 128/419 F |
| 4,600,010 A | 7/1986 | Dugot | 128/419 |
| 4,683,873 A | 8/1987 | Cadossi et al. | 128/1.5 |
| 5,014,699 A | 5/1991 | Pollack et al. | 128/419 |
| 5,038,797 A | 8/1991 | Batters | 128/798 |
| 5,269,746 A | 12/1993 | Jacobson | 600/13 |
| 5,273,033 A | 12/1993 | Hoffman | 607/46 |
| 5,338,286 A | 8/1994 | Abbott et al. | 600/14 |
| 5,374,283 A | 12/1994 | Flick | 607/46 |
| 5,743,844 A | 4/1998 | Tepper et al. | 600/14 |
| 5,968,527 A | 10/1999 | Litovitz | 424/400 |
| 6,083,149 A | 7/2000 | Wascher et al. | 600/9 |
| 6,132,362 A | 10/2000 | Tepper et al. | 600/14 |
| 6,186,940 B1 | 2/2001 | Kirschbaum | 600/12 |
| 6,261,221 B1 | 7/2001 | Tepper et al. | 600/14 |
| 6,485,963 B1 | 11/2002 | Wolf et al. | 435/298.2 |
| 6,605,089 B1 | 8/2003 | Michelson | 606/61 |
| 6,747,004 B1 | 6/2004 | Tabibzadeh | 514/12 |
| 2002/0052634 A1 | 5/2002 | March | 607/50 |
| 2003/0211084 A1 | 11/2003 | Brighton et al. | 424/93.7 |
| 2003/0233124 A1* | 12/2003 | Hara et al. | 607/3 |
| 2004/0006373 A1* | 1/2004 | Brighton et al. | 607/1 |
| 2004/0040233 A1* | 3/2004 | Park | 52/223.8 |

OTHER PUBLICATIONS

Bassett, C.A.L., "Low energy pulsing electromagnetic fields modify biomedical processes," *BioEssays*, 1987, 6(1), 36-42.

Bassett, C.A.L., et al., "Effects of pulsed electromagnetic fields on Steinberg ratings of femoral head osteonecrosis," *Clin. Orthop.*, Sep. 1989, 246, 172-185.

Bassett, C.A.L., et al., "Fundamental and practical aspects of therapeutic uses of pulsed electromagnetic fields (PEMSs)," *Crit. Rev. Biomed. Eng.*, 1989, 17(5), 451-529.

Bassett, C.A.L., et al., "Pulsing electromagnetic field treatment in ununited fractures and failed arthrodeses," *JAMA*, Feb. 5, 1982, 247(5), 623-628.

Binder, A., et al., "Pulsed electromagnetic field therapy of persistent rotator cuff tendonitis," *Lancet*, Mar. 31, 1984, 695-698.

Brighton, C.T., et al., "A multicenter study of the treatment of non-union with constant direct current," *J. Bone and Joint Surgery*, Jan. 1981, 62-A(1), 2-13.

Brighton, C.T., et al., "Treatment of recalcitrant non-union with a capacitively coupled electrical field," *J. Bone and Joint Surgery*, Apr. 1985, 67-A(4), 577-585.

Brighton, C.T., et al., "Treatment of castration-induced osteoporosis by a capacitively coupled electrical signal in rat vertebrae," *J. Bone and Joint Surgery*, Feb. 1989, 71-A(2), 228-236.

Brighton, C.T., et al., "Increased cAMP production after short-term capacitively coupled stimulation in bovine growth plate chrondrocytes," *J. Orthop. Res.*, 1988, 6, 552-558.

Brighton, C.T., et al., "Treatment of denervation/disuse osteoporosis in the rat with a capacitively coupled electrical signal: effects on bone formation and bone resorption," *J. Orthop. Res.*, 1988, 6, 676-684.

Goodman, R., et al., "Exposure of salivary gland cells to low-frequency electromagnetic fields alters polypeptide synthesis," *Proc. Natl. Acad. Sci. USA*, Jun. 1988, 85, 3928-3932.

Goodwin, C.B., et al., "A double-blind study of capacitively coupled electrical stimulation as an adjunct to lumbar spinal fusions," *Spine*, 1999, 24(13), 1349-1356.

Grodzinsky, A.J., "Electromechanical and physiochemical properties of connective tissue," *Crit. Rev. Biomed. Engng.*, 1983, 9(2), 133-198.

Harrison, M.H.M., et al., "Use of pulsed electromagnetic fields in perthes disease: report of a pilot study," *J. Pediatr. Orthop.*, 1984, 4, 579-584.

Jones, D.B., et al., "PEMF effects on differentiation and division in mirine melanoma cells are mediated indirectly through cAMP," *Trans. BRAGS 6*, 1986, 51.

Lorich, D.G., et al., "Biochemical pathway mediating the response of bone cells to capacitive coupling," *Clin. Orthop. and Related Res.*, 1998, 350, 246-256.

Massardo, L., et al., "Osteoarthritis of the knee joint: an eight year prospective study," *Ann Rheum Dis.*, 1989, 48, 893-897.

Mooney, V., "A randomized double-blind prospective study of the efficacy of pulsed electromagnetic fields for inter body lumbar fusions," *Spine*, 1990, 15(7), 708-712.

Norton, L.A., et al., "Pulsed electromagnetic fields alter phenotypic expression in chondroblasts in tissue culture," *J. Orthop. Res.*, 1988, 6, 685-689.

Rodan, G.A., et al., "DNA synthesis in cartilage cells is stimulated by oscillating electric fields," *Science*, Feb. 10, 1978, 199, 690-692.

Ryaby, J.T., et al., "Pulsing electromagnetic fields affect the phosphorylation and expression of oncogene proteins," *Trans. BRAGS 6*, 1986, p. 78.

Ryaby, J.T., et al., "The effect of electromagnetic fields on protein phosphorylation and synthesis in murine melanoma cells," *BRAGS*, p. 32.

Wang, W., et al., "The increased level of PDGF-A constributes to the increased proliferation induced by mechanical stimulation in osteoblastic cells," *Biochem. And Molecular Biol. International*, Oct. 1997, 43(2), 339-346.

Zhuang, H., et al., "Mechanical strain-induced proliferation of osteoblastic cells parallels increased TGF-$\beta$1 mRNA," *Biochem. Biophys. Res. Commun.*, 1996, 229, 449-453.

Zhuang, H., et al., "Electrical stimulation induces the level of TGF-$\beta$1 mRNA in osteoblastic cells by a mechanism involving calcium/calmodulin pathway," *Biochem. Biophys. Res. Commun.*, 1997, 237, 225-229.

Brighton, C.T., et al., "Fracture healing in the rabbit fibula when subjected to various capacitively coupled electrical fields," *J. Orthop. Res.*, 1985, 3, 331-340.

Brighton, C.T., et al., "*In vitro* bone-cell response to a capacitively coupled electrical field," *Clin. Orthop. Related Res.*, Dec. 1992, 285, 255-262.

Carter, E.L., et al., "Field distributions in vertebral bodies of the rat during electical stimulation: a parametric study," *IEEE Trans. on Biomed. Eng.*, Mar. 1989, 36(3), 333-345.

Brighton, C.T., et al., "Prevention and treatment of sciatic denervation disuse osteoporosis in rat tibia with capacitively coupled electrical stimulation," *Bone*, 1985, 6, 87-97.

Brighton, C.T., et al., "Treatment of nonunion of the tibia with a capacitively coupled electrical field," *J. of Trauma*, 1984, 24(2), 153-155.

Brighton, C.T., et al., "Tibial nonunion treated with direct current, capacitive coupling, or bone graft," *Clin. of Orthop. and Related Res.*, 1995, 321, 223-234.

Brighton, C.T., et al., "Signal transduction in electrically stimulated bone cells," *J. Bone Joint Surg. Am.*, 2001, 83-A(10), 1514-1523.

Pienkowski, D., et al., "Low-power electromagnetic stimulation of osteotomized rabbit fibuioe," *J. of Bone & Joint Surgery*, 1994, 76-A(4), 489-501.

Wang, W., et al., "Up-regulation of chondrocyte matrix genes and products by electric fields," *Clin. Orthopaedics & Related Res.*, 2004, 427S. S163-S173.

\* cited by examiner

ANATOMIC MODEL

ANALYTICAL MODEL

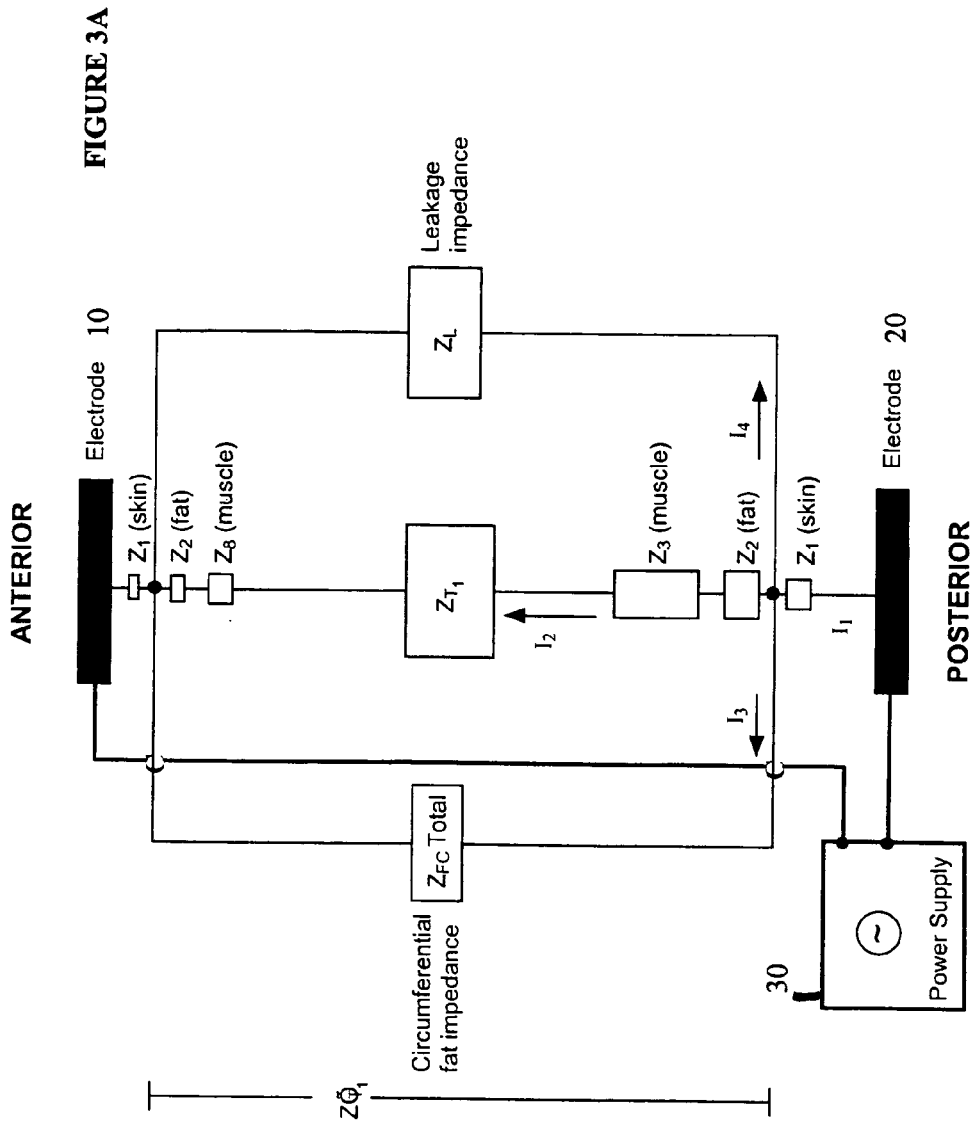

PLANAR CIRCUIT MODEL SHOWING $Z_{T_1}$ DETAIL FROM FIGURE 3A

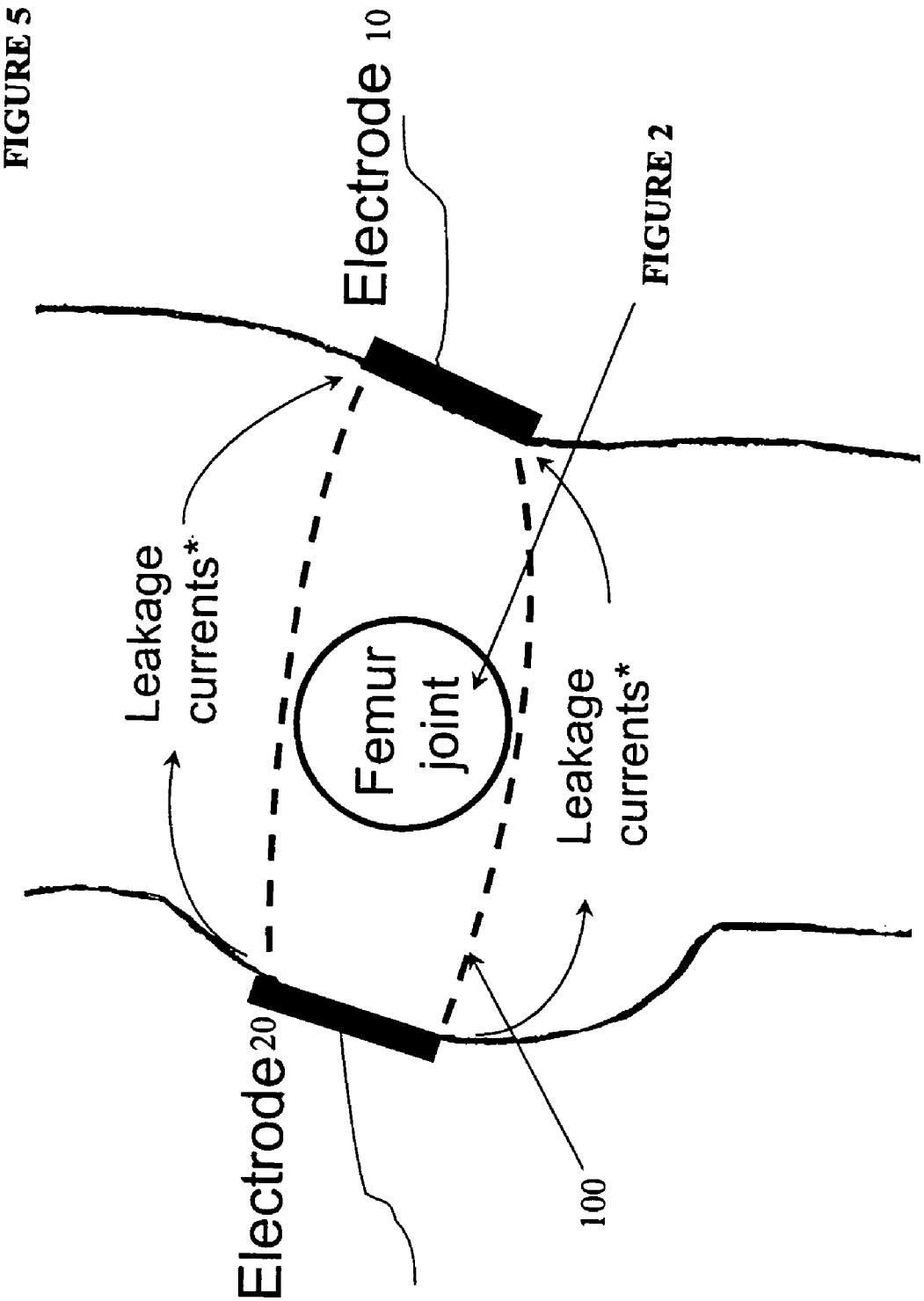

METHOD AND DEVICE FOR TREATING OSTEOARTHRITIS AND CARTILAGE DISEASE, DEFECTS, AND INJURIES IN THE HUMAN HIP

CROSS-REFERENCE TO RELATED APPLICATIONS

The present patent application claims priority to U.S. Provisional Patent Application Nos. 60/520,088 filed Nov. 14, 2003 and 60/535,734 filed Jan. 9, 2004. The present patent application also claims priority to U.S. patent application Ser. No. 10/257,126, filed Oct. 8, 2002, entitled "Regulation of Genes Via Application of Specific and Selective Electrical and Electromagnetic Signals", which claims priority to PCT/US01/05991 filed Feb. 23, 2001, and U.S. Provisional Application No. 60/184,491 filed Feb. 23, 2000, and U.S. patent application Ser. No. 10/255,241, filed Sep. 26, 2002, entitled "Regulation of Aggrecan Gene Expression with a Specific and Selective Electrical Signal", Ser. No. 10/267,708, filed Oct. 9, 2002, entitled "Regulation of Type II Collagen Gene Expression with a Specific and Selective Electrical Signal", Ser. No. 10/457,167, filed Jun. 9, 2003, entitled "Method and Apparatus for Treating Osteoarthritis, Cartilage Disease, Defects and Injuries in the Human Knee Joint," Ser. No. 10/461,188, filed Jun. 13, 2003, entitled "Regulation of Matrix Metalloproteinase Gene Expression Using Specific and Selective Electrical and Electromagnetic Signals," and Ser. No. 10/603,226, filed Jun. 25, 2003, entitled "Portable Electrotherapy Device for Treating Osteoarthritis and Other Diseases, Defects and Injuries of the Knee Joint." The contents of all of these applications are hereby incorporated by reference in their entireties.

FIELD OF THE INVENTION

The present invention is directed to a method of determining the voltage and current output required for the application of specific and selective electric and electromagnetic signals to diseased articular cartilage in the treatment of osteoarthritis, cartilage defects due to trauma or sports injuries, or as an adjunct with other therapies (e.g., cell transplantation, tissue-engineered scaffolds, growth factors, etc.) for treating cartilage defects in the human hip joint and a device for delivering such signals to a patient's hip.

BACKGROUND OF THE INVENTION

The bioelectrical interactions and activity believed to be present in a variety of biological tissues and cells are one of the least understood of the physiological processes. However, there has recently been much research into these interactions and activities related to the growth and repair of certain tissues and cells. In particular, there has been considerable interest in stimulation by electric and electromagnetic fields and their effect on the growth and repair of bone and cartilage. Scientists believe that such research might be useful in the development of new treatments for a variety of medical problems.

Osteoarthritis, also known as degenerative joint disease, is characterized by degeneration of articular cartilage as well as proliferation and remodeling of subchondral bone. The usual symptoms are stiffness, limitation of motion, and pain. Osteoarthritis is the most common form of arthritis, and prevalence rates increase markedly with age. It has been shown that elderly patients with self-reported osteoarthritis visit doctors twice as frequently as their unaffected peers. Such patients also experience more days of restricted activity and bed confinement compared to others in their age group. In one study, the majority of symptomatic patients became significantly disabled during an 8-year follow-up period (Massardo et al., Ann Rheum Dis 48:893–897, 1989).

Nonsteroidal anti-inflammatory drugs (NSAIDs) remain the primary treatment modality for osteoarthritis. It is unknown whether the efficacy of NSAIDs is dependent upon their analgesic or anti-inflammatory properties or the slowing of degenerative processes in the cartilage. There is also a concern that NSAIDs may be deleterious to patients. For example, NSAIDs display well-known toxic effects in the stomach, gastrointestinal tract, liver and kidney. Moreover, aspirin inhibits proteoglycan synthesis and normal cartilaginous repair processes in animals. One study in humans also suggested that indomethacin might accelerate breakdown of hip cartilage. All adverse effects appear more commonly in the elderly—the very population most susceptible to osteoarthritis.

In the disease commonly known as osteoporosis, bone demineralizes and becomes abnormally rarefied. Bone comprises an organic component of cells and matrix as well as an inorganic or mineral component. The cells and matrix comprise a framework of collagenous fibers that is impregnated with the mineral component of calcium phosphate (85%) and calcium carbonate (10%) that imparts rigidity to bone. While osteoporosis is generally thought to afflict the elderly, certain types of osteoporosis may affect persons of all ages whose bones are not subject to functional stress. In such cases, patients may experience a significant loss of cortical and cancellous bone during prolonged periods of immobilization. Elderly patients are known to experience bone loss due to disuse when immobilized after fracture of a bone; this may ultimately lead to a secondary fracture in an already osteoporotic skeleton. Diminished bone density may lead to collapse of vertebrae, fractures of hips, lower arms, wrists and ankles, as well as incapacitating pains. Alternative non-surgical therapies for such diseases are needed.

Pulsed electromagnetic fields (PEMFs) and capacitive coupling (CC) have been used widely to treat non-healing fractures and related problems in bone healing since approval by the Food and Drug Administration in 1979. The original basis for the trial of this form of therapy was the observation that physical stress on bone causes the appearance of tiny electric currents that, along with mechanical strain, were thought to be the mechanisms underlying transduction of the physical stress into a signal that promotes bone formation. Along with direct electric field stimulation that was successful in the treatment of nonunion bone fractures, noninvasive technologies using PEMF and CC (where the electrodes are placed on the skin in the treatment zone) were also found to be effective. PEMFs generate small, induced currents (Faraday currents) in the highly conductive extracellular fluid, while CC directly causes currents in the tissues; both PEMFs and CC thereby mimic endogenous electrical currents.

The endogenous electrical currents, originally thought to be due to phenomena occurring at the surface of crystals in the bone, have been shown to be due primarily to movement of fluid containing electrolytes in channels of the bone containing organic constituents with fixed negative charges, generating what are called "streaming potentials." Studies of electrical phenomena in cartilage have demonstrated a mechanical-electrical transduction mechanism that resembles those described in bone, appearing when cartilage is mechanically compressed, causing movement of fluid and electrolytes over the surface of fixed negative charges in the proteoglycans and collagen in the cartilage matrix. These streaming potentials apparently serve a purpose in cartilage similar to that in bone, and, along with mechanical strain, lead to signal transduction that is capable of stimulating chondrocyte synthesis of matrix components.

The main application of direct current, CC, and PEMFs has been in orthopaedics in the healing of nonunion bone fractures (Brighton et al. *J Bone Joint Surg* 1981;63:2–13; Brighton and Pollack *J Bone Joint Surg* 1985;67:577–585; Bassett et al. *Crit Rev Biomed Eng* 1989;17:451–529; Bassett et al. *J Am Med Assoc* 1982;247:623–628). Clinical responses have been reported in avascular necrosis of hips in adults and Legg-Perthe's disease in children (Bassett et al. *Clin Orthop* 1989;246:172–176; Aaron et al. *Clin Orthop* 1989;249:209–218; Harrison et al. *J Pediatr Orthop* 1984; 4:579–584, 1984). It has also been shown that PEMFs (Mooney. *Spine* 1990;15:708–712) and CC (Goodwin et al. *Spine* 1999;24:1349–135) can significantly increase the success rate of lumbar fusions. There are also reports of augmentation of peripheral nerve regeneration and function and promotions of angiogenesis (Bassett. *Bioessays* 1987; 6:36–42). Patients with persistent rotator cuff tendonitis refractory to steroid injection and other conventional measures showed significant benefit compared with placebo treated patients (Binder et al. *Lancet* 1984;695–698). Finally, Brighton et al., have shown in rats the ability of an appropriate CC electric field to both prevent and reverse vertebral osteoporosis in the lumbar spine (Brighton et al. *J Orthop Res* 1988;6:676–684; Brighton et al. *J Bone Joint Surg* 1989;71:228–236).

More recently, research in this area has focused on the effects that stimulation has on tissues and cells. For example, it has been conjectured that direct currents do not penetrate cellular membranes and that control is achieved via extracellular matrix differentiation (Grodzinsky *Crit Rev Biomed Eng* 1983;9:133). In contrast to direct currents, it has been reported that PEMFs can penetrate cell membranes and either stimulate them or directly affect intracellular organelles. An examination of the effect of PEMFs on extracellular matrices and in vivo endochondral ossification found increased synthesis of cartilage molecules and maturation of bone trabeculae (Aaron et al. *J Bone Miner Res* 1998;4:227–233). More recently, it was reported (Lorich et al. *Clin Orthop Related Res* 1998;350:246–256) that signal transduction of a capacitively coupled electric signal is via voltage-gated calcium channels, leading to an increase in cytosolic calcium with a subsequent increase in activated (cytoskeletal) calmodulin.

Much research has been performed using tissue culture techniques in order to understand the mechanisms of response. In one study, it was found that electric fields increased [$^3$H]thymidine incorporation into the DNA of chondrocytes, supporting the notion that $Na^+$ and $Ca^{+2}$ fluxes generated by electrical stimulation trigger DNA synthesis (Rodan et al. *Science* 1978;199:690–692). Studies have found changes in the second messenger, cAMP, and cytoskeletal rearrangements due to electrical perturbations (Ryaby et al. *Trans BRAGS* 1986;6; Jones et al. *Trans. BRAGS* 6:51, 1986; Brighton and Townsend *J Orthop Res* 1988;6:552–558). Other studies have found effects on glycosaminoglycan, sulfation, hyaluronic acid, lysozyme activity and polypeptide sequences (Norton et al. *J Orthop Res* 1988;6:685–689; Goodman et al. *Proc Natl Acad Sci* 1988; 85:3928–3932).

It was reported in 1996 by one of the present inventors that a cyclic, biaxial 0.17% mechanical strain produces a significant increase in TGF-$\beta_1$ mRNA in cultured MC3T3-E1 bone cells (Zhuang et al. *Biochem Biophys Res Commun* 1996;229:449–453). Several significant studies followed in 1997. In one study it was reported that the same cyclic, biaxial 0.17% mechanical strain produced a significant increase in PDGF-A mRNA in similar bone cells (Wang et al. *Biochem Mol Biol Int* 1997;43:339–346). It was also reported that a 60 kHz capacitively coupled electric field of 20 mV/cm produced a significant increase in TGF-$\beta_1$ mRNA in similar bone cells (Zhuang et al. *Biochem Biophys Res Commun* 1997;237:225–229). However, the effect such a field would have on other genes has not been reported in the literature.

In the above-referenced parent patent application, entitled "Regulation of Genes Via Application of Specific and Selective Electrical and Electromagnetic Signals," methods were disclosed for determining the specific and selective electrical and electromagnetic signals for use in creating specific and selective fields for regulating target genes of diseased or injured tissues. The present invention builds upon the technique described therein by describing the method of determining the voltage and current output required, and the corresponding apparatus for delivering specific and selective electrical and electromagnetic signals to the human hip joints in patients afflicted with osteoarthritis and other cartilage defects, diseases and injuries.

SUMMARY OF THE INVENTION

The present invention related to treating osteoarthritis and other cartilage diseases, defects, and injuries in human hip joints via the application of specific and selective fields generated by specific and selective electric and/or electromagnetic signals. The invention includes a method of determining the voltage and current of the signal to apply to electrodes or to a solenoid or to at least one coil applied to the hip for treatment.

More particularly, the invention relates to a method of treating diseased tissue in a human through the application of a specific and selective electric or electromagnetic field to diseased tissue in a human, including osteoarthritis and other cartilage diseases, defects and injuries in the hip, or used as an adjunct with other therapies (cell transplantation, tissue-engineered scaffolds, growth factors, etc.) in treating cartilage defects in the human hip. The method includes the steps of determining the voltage and current output that produces the desired 20 mV/cm electric field in the articular cartilage of the human hip joint, and other voltage and current values for other effective electric field amplitudes thought or known to be effective. The method includes constructing an anatomic model of the human hip joint and translating the anatomic model to an analytical model of the hip in which the dimensions for the tissues encountered from skin (anterior) through fat and skin (posterior) are determined. Planar circuits were then constructed in which the various tissue conductivities, impedances and current flow were used in calculating the voltage and current required to be applied to surface electrodes placed anteriorly and posteriorly on the skin covering the hip in order to produce an electric field at 20 mV/cm in articular cartilage of the hip joint at a frequency of 60 kHz. One knowledgeable in the field could perform the same analysis at other frequencies, adjust the tissue impedances to their values at the new frequency and obtain different values for the ranges of the electrical field and current density at any chosen frequency or set of frequencies.

The invention also includes a method and a device for treating diseased tissue (such as osteoarthritis), defective or injured tissue in a human hip joint through the application of a specific and selective electric or electromagnetic field to the afflicted tissue in the human hip joint. Such a device in accordance with a capacitive coupling embodiment of the invention includes at least two electrodes adapted for application in the proximity of a patient's hip joint and a signal generator that generates electric signals for application to the electrodes so as to produce an electric field of amplitude of 20 mV/cm±15% and a current density of 120 $\mu$A/cm$^2$±15% within the synovium and articular cartilage of the patient's hip joint. An inductive coupling embodiment of the invention includes a coil(s) or solenoid adapted and configured to receive the electric signals to produce these electric fields. Preferably, the signal generator provides one of a plurality of output electric signals with a voltage selected by a user in accordance with a size of the human hip joint. Larger hip joints receive signals of larger voltages.

These and other aspects of the present invention will be elucidated in the following detailed description of the invention.

BRIEF DESCRIPTION OF THE DRAWINGS

The present invention will be apparent from the following detailed description of the invention in conjunction with the accompanying drawings, of which:

FIG. 3A illustrates a planar circuit model of the human hip joint showing circumferential flow of current through the fat layers ($I_3$) plus leakage flow of current through the muscle and other soft tissue ($I_4$), plus current flow across the hip joint ($I_2$) and the impedance (Z) compartments.

FIG. 5 illustrates electrode placement on the skin that is required to produce the desired electric field in the hip joint.

DETAILED DESCRIPTION OF ILLUSTRATIVE EMBODIMENTS

The invention will be described with reference to FIGS. 1–5 and Tables 1–3. Those skilled in the art will appreciate that the description given herein with respect to these figures is for exemplary purposes only and is not intended in any way to limit the scope of the invention. All questions regarding the scope of the invention may be resolved by referring to the appended claims.

Definitions:

As used herein, the term "signal" is used to refer to a variety of signals including mechanical signals, ultrasound signals, electromagnetic signals, and electric signals outputted by a device.

As used herein, the term "field" refers to an electric field within a targeted tissue, whether it is a combined field or a pulsed electromagnetic field, or generated by direct current, capacitive coupling, or inductive coupling.

Determination of Voltage and Current:

Previous studies by the present inventors have shown that a capacitively coupled field significantly increased the proliferation of bone cells grown in culture (Brighton, Pollack, et al, V. Orthop. Research, 3:331–340, 1985) and significantly increased the rate of healing in a rat fractured fibula model (Brighton, Pollack, et al, Clin. Orthop. And Related Research, 285:255–262, 1992). Also, the field distributions in the vertebral bodies of rats during capacitively coupled electrical stimulation have been determined (Carter, Vresilovic, Pollack, and Brighton, IEEE transactions on Biomedical Engineering, 36(–3): 333–3345,1989). In order to determine the required output voltage and current required to produce an equivalent electric field and current density in a human hip joint, the analytical model depicted in FIG. 2 was developed in accordance with the invention for representing the typical human hip joint illustrated in FIG. 1.

Figure 1:
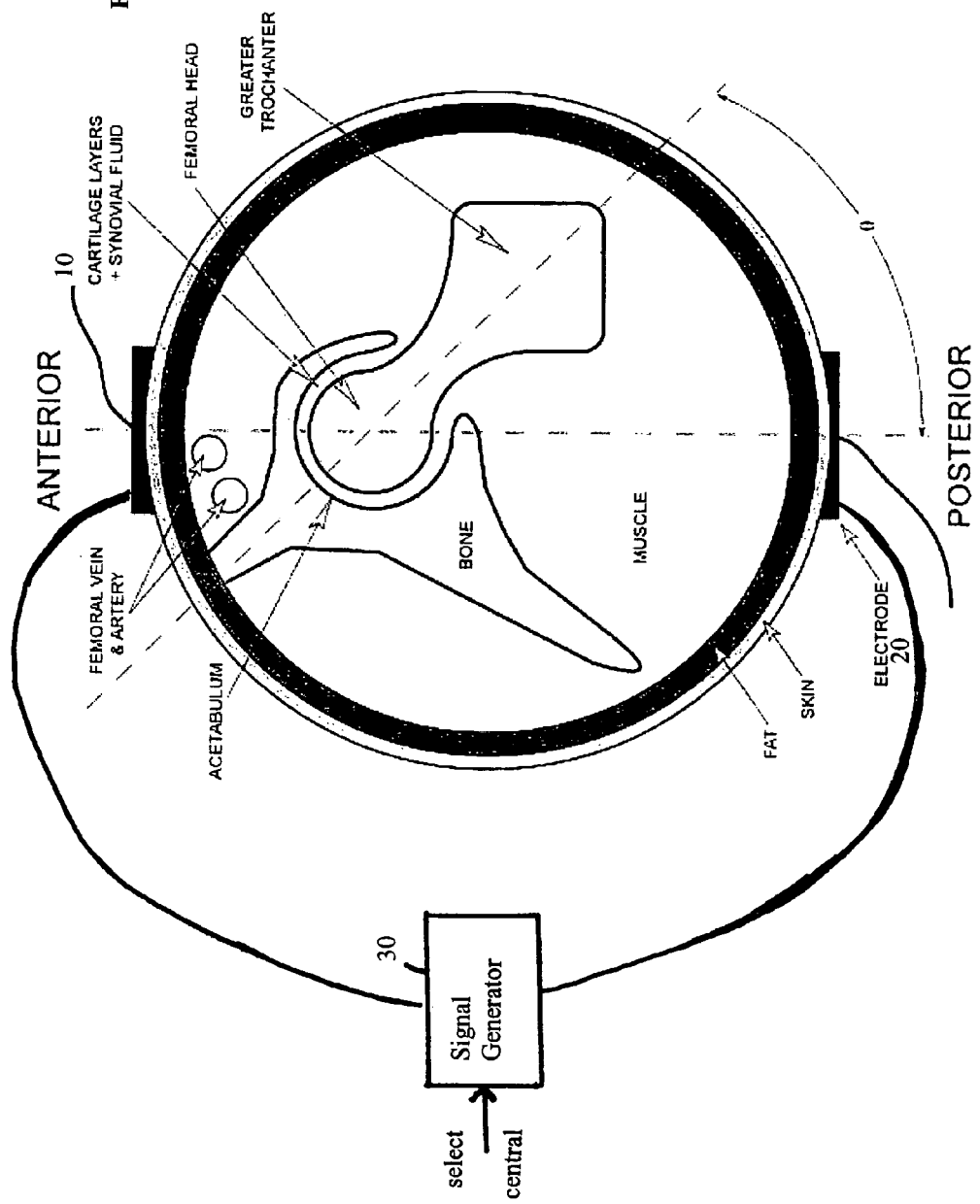
FIG. 1 illustrates an anatomic model of the human hip joint showing all the important tissues and structures through which the current passes between the anterior and posterior surface electrodes placed on skin.

As shown in FIG. 1, the typical human hip joint includes layers of cartilage and synovial fluid that is bounded by the acetabulum and the femoral head. In accordance with the invention, osteoarthritis, cartilage disease, defects and injuries in the hip joint is treated by the application of specific and selective electric fields via electrodes 10, 20 attached relative to the hip joint substantially as shown in FIG. 1. A signal generator 30 provides the appropriate signals to the electrodes for generating the specific and selective electric fields. The specific and selective electric field needed to treat osteoarthritis, cartilage disease, defects and injuries in the hip joint is calculated in accordance with the invention using the analytical model of the hip joint depicted in FIG. 2.

FIG. 1 illustrates an anatomical model for use in determining the electric field amplitude and current density obtained in the cartilage space in a hip joint when electrodes 10, 20 are placed anteriorly and posteriorly, respectively, and a voltage is applied causing a current to flow through the body. In the analytical model of FIG. 2, the following elements are identified as indicated: electrodes 10, 20, skin 40, fat 50, muscle 60, bone (acetabulum) 70, cartilage and synovial fluid 80, and femoral head 90. In an exemplary embodiment, the frequency of a sine wave voltage is taken to be 60 kHz; however, the methodology described herein can be applied to any frequency as long as the electrical properties of the tissues are chosen for those frequencies. It is desired to determine the voltage and the current to be applied to the electrodes 10, 20 in order to obtain in the cartilage of the hip joint a therapeutic electric field amplitude of 20 mV/cm in a preferred embodiment, and voltage and current values for other effective electric field amplitudes known to be effective.

Figure 2:
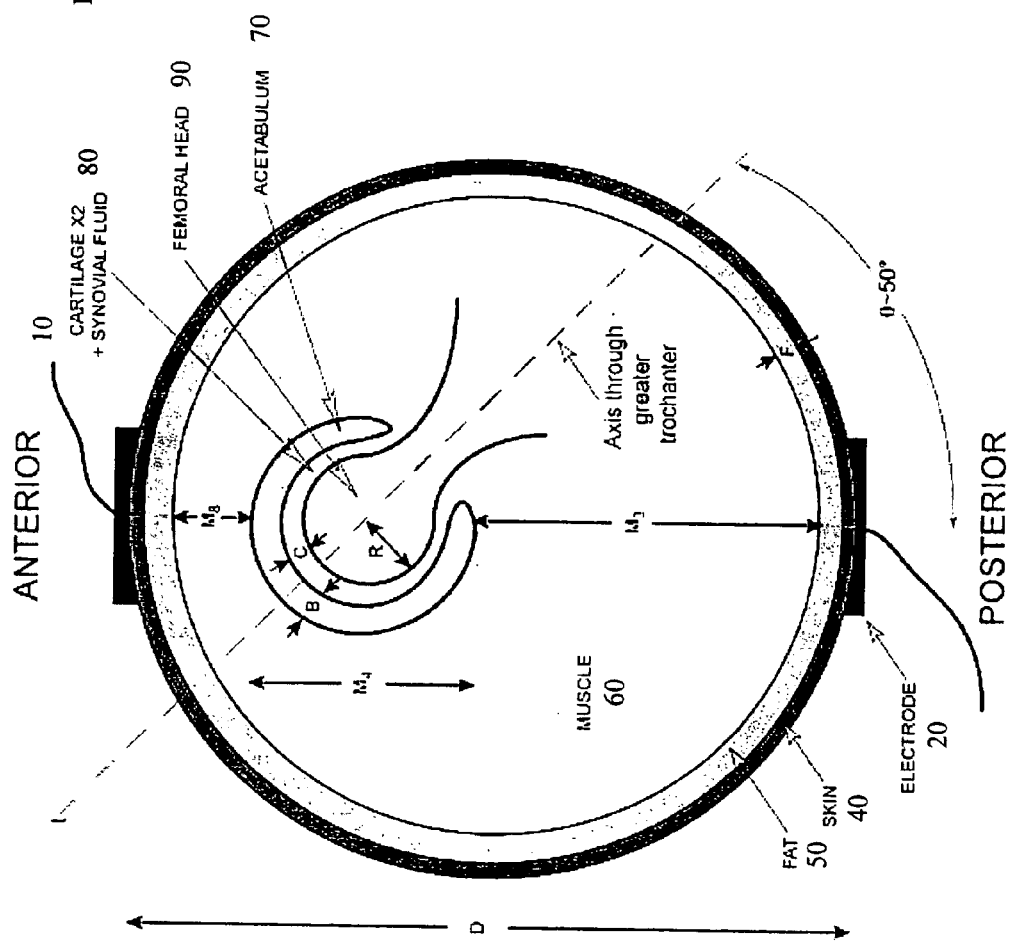
FIG. 2 illustrates an analytical model of the human hip joint from which size parameters are determined for each of the tissues and structures indicated.
Figure 3B:
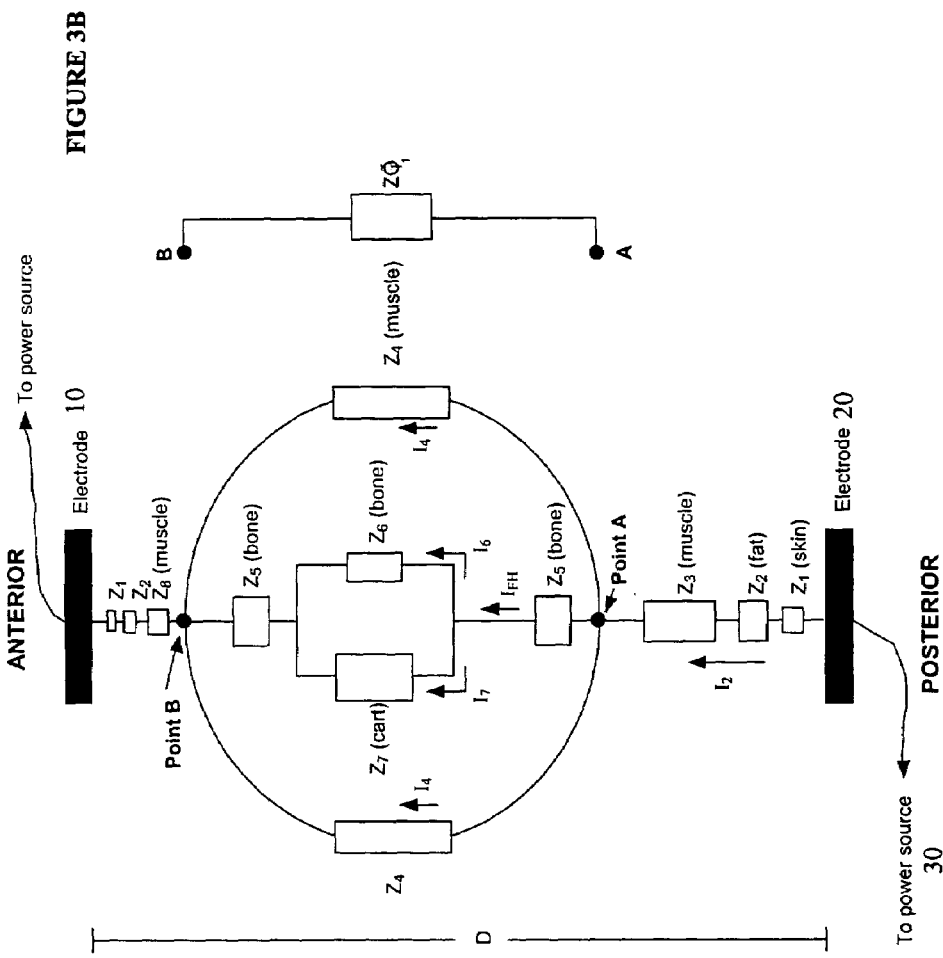
FIG. 3B illustrates a planar circuit showing in detail the current flow and impedances across the hip joint ($Z_{T1}$).
Figure 4:
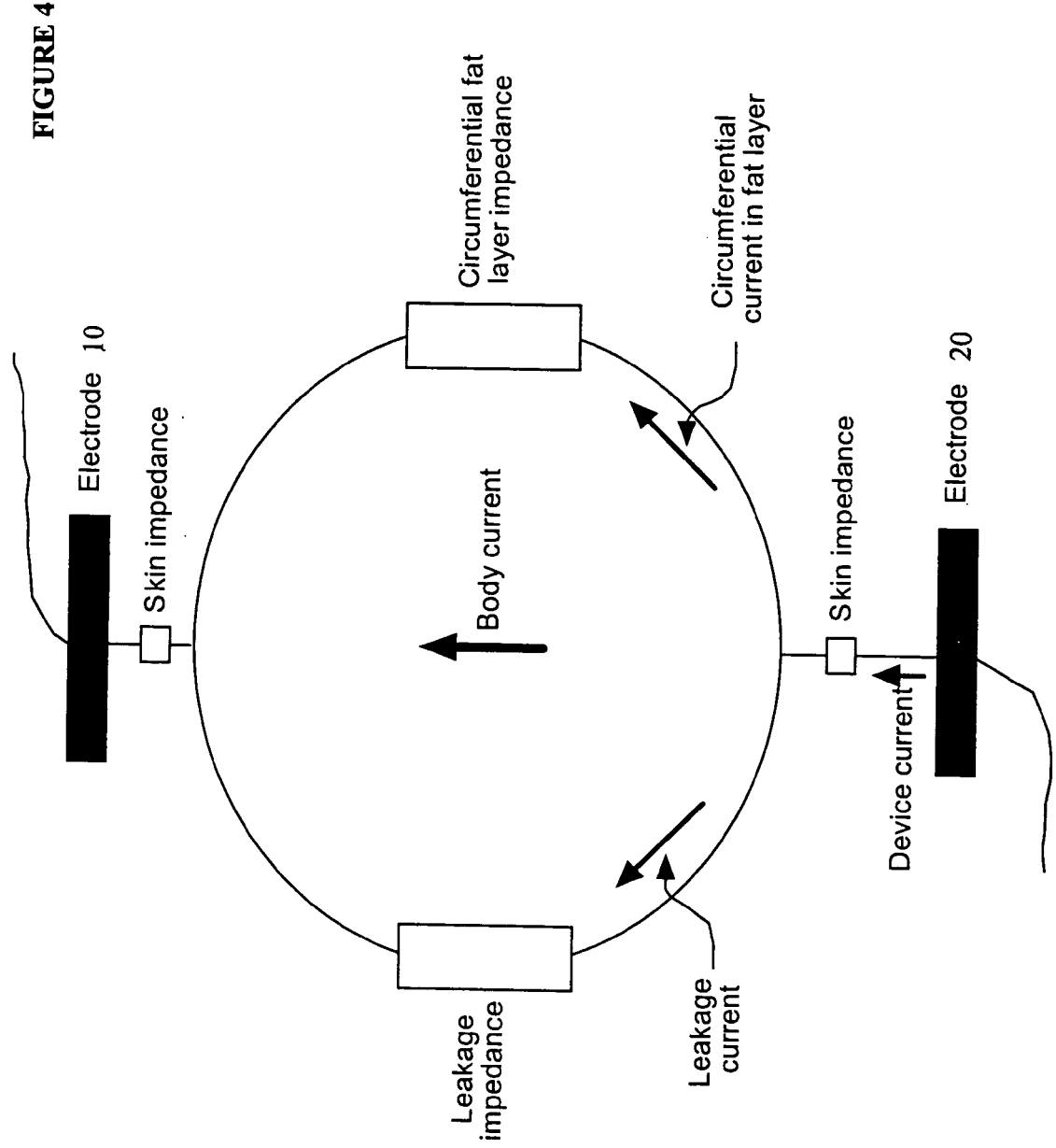
FIG. 4 illustrates schematically the three currents that were calculated in determining the output current and voltage required to produce a 20 mV/cm field in the articular cartilage of the hip joint. The three currents are the circumferential current, the leakage current, and the current flowing through the hip joint.

It is clear from FIGS. 1 and 2 that patients of different sizes may require different applied voltages and currents to achieve the therapeutic electric field amplitudes. Accordingly, the calculation in accordance with the invention will model the patient for four (4) different size classifications. The essential geometric model parameters for these four sizes along with the relevant electrical properties of all tissue types are shown below in Tables 1A and 1B with reference to the distances illustrated in FIG. 2. The electrodes 10, 20 are assumed to be 2"×2" square and the currents are calculated by considering the current flow through the patient's body for a 2"×2" rectangle from one electrode to the other plus the circumferential flow of current through the fat layer plus the leakage current that flows through the muscle and other soft tissues outside of the 2"×2" rectangle but excluding the circumferential current in the fat layer. These currents are shown in FIGS. 3 and 4. The impedances of the tissue compartments through which the current $I_2$ (FIG. 3)

flows are shown in FIG. 3B. A line drawing showing patient electrode placement is presented in FIG. 5. In FIG. 5, the region in broken lines is modeled as a 2"×2" rectangle 100 in which the body current is assumed to flow. Leakage currents as shown in FIGS. 3A and 4 include circumferential flow in the fat layer and body currents outside of the 2"×2" rectangle 100. The current flow and impedance through region 100 are those shown in FIG. 3B.

TABLE 1A

Size Parameters for Four Patient Classifications

| Measurement | Patient Classification | | | |
|---|---|---|---|---|
| | Small (m) | Medium (m) | Large (m) | Extra-Large (m) |
| Electrode-to electrode distance (D*) | 0.1524 | 0.18 | 0.21 | 0.305 |
| Fat layer thickness (F*) | 0.00635 | 0.00762 | 0.0222 | 0.699 |
| Fat layer width | 0.051 | 0.051 | 0.051 | 0.051 |
| Muscle ($M_3$*) length | 0.051 | 0.0635 | 0.0635 | 0.0635 |
| Muscle ($M_3$*) width | 0.051 | 0.051 | 0.051 | 0.051 |
| Muscle ($M_4$*) length | 0.0635 | 0.0762 | 0.0762 | 0.0762 |
| Muscle ($M_4$*) width | 0.0254 | 0.0254 | 0.0254 | 0.0254 |
| Muscle ($M_8$*) length | 0.0254 | 0.0254 | 0.0254 | 0.0254 |
| Muscle ($M_8$*) width | 0.051 | 0.051 | 0.051 | 0.051 |
| Cartilage junction length | 0.08 | 0.08 | 0.08 | 0.08 |
| Cartilage junction width | 0.0127 | 0.0127 | 0.0127 | 0.0127 |
| Femoral head radius (R*) | 0.0254 | 0.0254 | 0.0254 | 0.0254 |
| Acetabular thickness (B*) | 0.015 | 0.015 | 0.015 | 0.015 |
| Acetabular width | 0.04 | 0.04 | 0.04 | 0.04 |

*See FIG. 2

TABLE 1B

Electrical Conductivities

| TISSUE | CONDUCTIVITY |
|---|---|
| Fat | 0.02 S/m |
| Muscle | 0.45 S/m |
| Bone | 0.01 S/m |
| Cartilage | 0.6 S/m |
| Skin Admittance | $3 \times 10^{-3}$ S/cm² |

The definitions of terms in FIGS. 2, 3A, 3B and 4 are shown below in Table 2. Each impedance labeled in FIGS. 3 and 4 was calculated using the relationship:

$$Z = \frac{1}{\sigma} \cdot \frac{Length}{Area} \quad \text{(Equation 1)}$$

Where Length is the dimension of the tissue in the direction of the current flow, Area is the cross-sectional area of the tissue perpendicular to the direction of current flow, and σ is the electrical conductivity.

TABLE 2

Definitions of dimensions and symbols shown in FIGS. 2 and 3

D = electrode to electrode distance
F = fat layer thickness
M = muscle:  $M_3$ = distance (thickness) of muscle from posterior fat layer to posterior acetabulum
  $M_4$ = distance (thickness) of muscle from posterior acetabulum to anterior acetabulum
  $M_8$ = distance (thickness) of muscle from anterior acetabulum to anterior fat layer TABLE 2-continued Definitions of dimensions and symbols shown in FIGS. 2 and 3

Z = impedance:  $Z_1$ = impedance of skin
  $Z_2$ = impedance of fat
  $Z_3$ = impedance of muscle posterior to the acetabulum
  $Z_4$ = impedance of the muscle around the hip joint
  $Z_{FH}$ { $Z_5$ = impedance of bone (acetabulum)
  $Z_6$ = impedance of bone (femoral head)
  $Z_7$ = impedance of articular cartilage-synovium
  $Z_8$ = impedance of muscle anterior to the acetabulum
  $Z_{T1}$ = impedance across the hip joint; i.e., the combined impedance from Point A to Point B in FIG. 3B I = current:  $I_{total}$ = total current flowing from electrode to electrode
  $I_{FH}$ = current flowing through hip joint
  $I_4$ = current flowing through muscle
  $I_6$ = current flowing through femoral head
  $I_7$ = current flowing through articular cartilage B = Bone (acetabulum) thickness
C = cartilage-synovium thickness
R = radius of femoral head
J = current density (A/cm²)
E = electric field (V/cm)

The impedances were then calculated using Equation 1, the dimensions in Table 1A and the conductivities in Table 1B. Using standard lump circuit analysis for series/parallel impedances, the total current, $I_1$ (FIG. 3A) that must flow from the electrodes was calculated for each patient classification for a voltage applied to the electrodes. In addition, $I_2$, the current flow through the muscle-femur-cartilage-muscle layers; the current $I_3$, the current flowing circumferentially through the fat layer and $I_4$, the leakage currents, were also calculated. This enabled the calculation of the current through the cartilage, $I_{cartilage}$, and the current density, $J_{cartilage}$, from which the electric field amplitude in the cartilage, $E_{cartilage}$ could be computed from the equation:

$$J_{cartilage} = \sigma_{cartilage} \cdot E_{cartilage} \quad \text{(Equation 2)}$$

where $J_{cartilage}$ and $E_{cartilage}$ are described above and $\sigma_{cartilage}$ is the electrical conductivity of the cartilage as shown in Table 1B. These results are summarized in Table 3A. From Table 3A, it is apparent that for an applied voltage of approximately 5 V peak-to-peak sine wave at 60 kHz, one obtains electric fields of 20 mV/cm±3.5 mV/cm for the small, medium and large patient, but not for the extra-large patient. The extra-large patient requires a voltage that is approximately twice that required for the other three patient sizes.

TABLE 3A

Device Voltage and Current Required to Apply 20 mV/cm Electric Field to Cartilage in the Human Hip

| Patient Size | Device Voltage | Device Current (2" × 2" electrode) | Electrode Current Density |
|---|---|---|---|
| Small | 4.3 $V_{p-p}$ | 26.8 mA | 1.04 mA/cm² |
| Medium | 4.5 $V_{p-p}$ | 31.6 mA | 1.23 mA/cm² |
| Large | 5.7 $V_{p-p}$ | 32.0 mA | 1.24 mA/cm² |
| Extra Large | 10.2 $V_{p-p}$ | 52.1 mA | 2.02 mA/cm² |

It is now possible to calculate the device current to the 2"×2" electrodes 10, 20 in order to achieve a 20 mV/cm electric field amplitude in the cartilage. These values, and the approximate device voltages that achieve these device currents are shown below in Table 3B along with the current and current density in the cartilage when the applied voltage is as shown for each patient size:

TABLE 3B

Cartilage Current and Current Density When a 20 mV/cm Electric Field is Applied to the Cartilage of the Human Hip

| Patient Size | Cartilage Current | Cartilage Current Density |
|---|---|---|
| Small | 0.15 mA | 120 μA/cm$^2$ |
| Medium | 0.15 mA | 120 μA/cm$^2$ |
| Large | 0.15 mA | 120 μA/cm$^2$ |
| Extra Large | 0.15 mA | 127 μA/cm$^2$ |

It is noted that for extra-large patients, the current density value at the electrodes, 2.02 mA/cm$^2$, is at the maximum value and should not be exceeded.

It is understood that patients with a specific size, i.e., electrode-to-electrode dimension, may have tissue compartment sizes and/or skin impedance values that differ from those modeled here. Therefore, devices that power the electrodes should have output variability to increase the peak-to-peak voltage to achieve the desired electrode current (density).

The current (or electric field) that flows through the cartilage of the hip when a voltage is applied to the electrodes on the skin is determined by the impedances shown in FIGS. 3A and 3B. For a given patient size, the dimensions of various tissue compartments (and therefore their impedances) can vary so that the current that actually flows through the cartilage could be higher or lower than the values shown for an applied device voltage as shown above. Taking reasonable variations in dimensions of the tissue compartments for each patient size, it may be determined that for a given device voltage, the cartilage current (and therefore the cartilage electric field) could differ by ±15%. Therefore, in order to account for this variation, and to account for the variation of skin electrical impedance from patient to patient, the device should be designed to apply the device current value plus or minus 15% to the pair of 2"×2" electrodes 10, 20.

Thus, in accordance with the invention, the approximate size of the patient's hip is determined, and a signal is generated and applied to the electrodes that will generate the desired electric field with a voltage of 20 mV/cm±15% and a current density of 120 μA/cm$^2$±15% within the synovium and articular cartilage for treatment of osteoarthritis in the hip, for example. Preferably, the signal generator includes a select control (FIG. 1) that allows the operator to select the proper output based on the size of the patient's hip.

Although implementations of the invention have been described in detail above, those skilled in the art will readily appreciate that many additional modifications are possible without materially departing from the novel teachings and advantages of the invention. For example, those skilled in the art will appreciate that the techniques of the invention may be applied to capacitive and inductive coupling systems. In the case of capacitive coupling, the scaled voltage and current are applied to the hip region using two electrodes as illustrated in FIGS. 1 and 2. On the other hand, in the case of inductive coupling, the scaled voltage and current are applied to the hip region using a solenoid or coil(s). Any such modifications are intended to be included within the scope of the invention as defined in the following claims.

What is claimed:

1. A method of treating disease tissue in a human through the application of a specific and selective electric or electromagnetic field to the disease tissue in the human, comprising the steps of:
   a. Determining the voltage and current output that produces a 20 mV/cm electric field in the diseased tissue of the human;
   b. Constructing an anatomic model of human diseased tissue showing all the pertinent tissues and structures through which the current passes between the skin overlying one side of the diseased tissue through the skin on the opposite side of the diseased tissue;
   c. Constructing an analytic model of the diseased tissue from which size parameters are determined for each of the tissues and structures through which the current passes between the anterior and posterior skin surfaces enclosing the diseased tissue;
   d. Constructing a planar circuit model of the diseased tissue giving the impedance and current flow in detail of all the structures and tissues through which the current must flow to achieve a 20 mV/cm electric field in the diseased tissue;
   e. Computing the electric field amplitude (20 mV/cm) in the diseased tissue as equal to the targeted diseased tissue current density divided by the targeted diseased tissue conductivity; and
   f. Applying the computed voltage and current to the diseased tissue of the human.

2. The method of claim 1 wherein the computed voltage and current applying step comprises the step of applying the computed voltage and current to the human using two electrodes in the case of capacitive coupling.

3. The method of claim 1 wherein the computed voltage and current applying step comprises the step of applying the computed voltage and current to the human using a solenoid or coil(s) in the case of inductive coupling.

4. The method of claim 1 wherein the voltage and current output determining step comprises the step of determining the voltage and current output that produces a 20 mV/cm electric field in the tissues of the diseased human hip.

5. The method of claim 4 wherein the anatomic model constructing step comprises the step of constructing an anatomic model of the human hip.

6. The method of claim 5 wherein the step of constructing an anatomic model of the diseased tissue comprises the step of constructing an analytic model of the diseased human hip from which size parameters are determined for each of the tissues and structures through which the current passes between anterior and posterior skin surfaces enclosing the human hip.

7. The method of claim 6 wherein the step of constructing the planar circuit model comprises the step of constructing a planar circuit model of the human hip in order to determine the circumferential flow of current through a fat layer, a leakage flow of current through muscle and other soft tissue, and current flow across and through the human hip.

8. The method of claim 7 wherein the step of constructing the planar circuit model comprises the step of constructing a planar circuit model of the human hip giving the impedance and current flow of all the tissues and structures through which the current must flow to achieve a 20 mV/cm electric field in the human hip.

9. The method of claim 8 wherein the step of computing the electric field amplitude comprises the step of computing the desired electric field amplitude (20 mV/cm) in the diseased human hip as equal to the current density in the tissues of the hip divided by the conductivity of the tissues in the hip.

10. The method of claim 1 wherein the computed voltage and current are applied to a diseased human hip.

11. A device for treating diseased tissue in the human hip joint through the application of a specific and selective electric or electromagnetic field to the diseased or injured tissue in the human hip joint comprising:
   a. one of (a) at least two electrodes, in the case of capacitive coupling, adapted for application in the proximity of a patient's hip joint; and (b) a solenoid or at least one coil, in the case of inductive coupling, adapted for application in the proximity of a patient's hip joint; and
   b. a signal generator adapted to generate electric signals for application to the electrodes, the solenoid, or at least one coil so as to cause the production of an electric field of approximately 20 mV/cm±15% and a current density range of approximately 120 µA/cm²±15% within the synovium and articular cartilage of the patient's hip joint for treatment of diseased tissue in the patient's hip joint.

12. A device as in claim 11, wherein the signal generator provides one of the plurality of output electric signals in accordance with a size of the human hip joint and its surrounding soft tissue and skin.

13. A device as in claim 12, wherein one of the plurality of output electrical signals of the signal generator for a 60 kHz frequency has a voltage of approximately 4.3 $V_{p-p}$±10% for a small size hip joint.

14. A device as in claim 12, wherein one of the plurality of output electrical signals of the signal generator for a 60 kHz frequency has a voltage of approximately 4.5 $V_{p-p}$±10% for a medium sized hip joint.

15. A device as in claim 12, wherein one of the plurality of output electrical signals of the signal generator for a 60 kHz frequency has a voltage of approximately 5.7 $V_{p-p}$±10% for a large sized hip joint.

16. A device as in claim 12, wherein one of the plurality of output electrical signals of the signal generator for a 60 kHz frequency has a voltage of approximately 10.2 $V_{p-p}$±10% for a extra large sized hip joint.

17. A device for treating osteoarthritis, cartilage defects due to trauma or sports injury, or used as an adjunct with other therapies for treating cartilage defects in a human hip joint through the application of specific and selective electric or electromagnetic field to the afflicted tissue in the human hip joint, comprising:
   a. one of (a) at least two electrodes on the surface of the skin and (b) a solenoid or at least one coil located external to the skin adapted for application in the proximity of a patient's hip joint; and
   b. a signal generator adapted to generate electric signals for application to the electrodes, the solenoid, or at least one coil so as to cause the production of an electric field of approximately 20 mV/cm±15% and a current density range of approximately 120 µA/cm²±15% within the synovium and articular cartilage of the patient's hip joint for treatment of diseased tissue in the patient's hip joint.

18. A device as in claim 17, wherein the signal generator provides one of the plurality of output electric signals in accordance with a size of the human hip joint and its surrounding soft tissue and skin.

19. A device as in claim 18, wherein one of the plurality of output electrical signals of the signal generator for a 60 kHz frequency has a voltage of approximately 4.3 $V_{p-p}$±10% for a small size hip joint.

20. A device as in claim 19, wherein one of the plurality of output electrical signals of the signal generator for a 60 kHz frequency has a voltage of approximately 4.5 $V_{p-p}$±10% for a medium sized hip joint.

21. A device as in claim 19, wherein one of the plurality of output electrical signals of the signal generator for a 60 KHz frequency has a voltage of approximately 5.7 $V_{p-p}$±10% for a large sized hip joint.

22. A device as in claim 19, wherein one of the plurality of output electrical signals of the signal generator for a 60 KHz frequency has a voltage of approximately 10.2 $V_{p-p}$±10% for a extra large sized hip joint.

23. A method of treating osteoarthritis in a human knee joint through the application of a specific and selective electric or electromagnetic field to the diseased tissue in the human knee joint, comprising the steps of:
   converting electric potential into an electric signal that when applied to one of (a) at least two electrodes on the surface of the skin and (b) a solenoid or at least one coil located external to the skin adapted for application in the proximity of a patient's hip joint, an electric field of not less than approximately 20 mV/cm±15% is produced and a current density of not less than approximately 120 µA/cm²±15% is produced within the synovium and articular cartilage of the patient's hip joint; and
   applying the electric signal to the at least two electrodes, solenoid or coil so as to produce the electric field within the synovium and articular cartilage of the patient's hip joint.

24. A method as in claim 23, comprising the additional step of selecting one of a plurality of output electric signals with a voltage in accordance with a size of the human hip joint.

25. A method as in claim 24, wherein the selecting step comprises the step of selecting an electrical signal having a voltage of approximately 4.3 $V_{p-p}$±10% for a small size hip joint.

26. A method as in claim 25, wherein the selecting step comprises the step of selecting an electrical signal having a voltage of approximately 4.5 $V_{p-p}$±10% for a medium sized hip joint.

27. A method as in claim 25, wherein the selecting step comprises the step of selecting an electrical signal having a voltage of approximately 5.7 $V_{p-p}$±10% for a large sized hip joint.

28. A method as in claim 25, wherein the selecting step comprises the step of selecting an electrical signal having a voltage of approximately 10.2 $V_{p-p}$±10% for a extra large sized hip joint.

* * * * *